US00PP19669P2

(12) United States Plant Patent
Hambali

(10) Patent No.: US PP19,669 P2
(45) Date of Patent: Feb. 3, 2009

(54) ***AGLAONEMA* PLANT NAMED 'TWYAG0009B'**

(50) Latin Name: *Aglaonema*
Varietal Denomination: TWYAG0009B

(75) Inventor: Gregori G. Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/903,061

(22) Filed: Sep. 20, 2007

(51) Int. Cl.
*A01H 5/00* (2006.01)

(52) U.S. Cl. ..... Plt./376
(58) Field of Classification Search ..... Plt./376
See application file for complete search history.

*Primary Examiner*—Anne Marie Grunberg
*Assistant Examiner*—Louanne C Krawczewicz
(74) *Attorney, Agent, or Firm*—Jondle & Associates, P.C.

(57) ABSTRACT

A new *Aglaonema* plant particularly distinguished by having a very dense, leafy, compact and upright branched growth habit, being small to intermediate in stature and very vigorous and having a somewhat faster growth rate than typical commercial *Aglaonema* cultivars is disclosed.

2 Drawing Sheets

Genus and species: *Aglaonema* hybrid.
Variety denomination: 'TWYAG0009B'.

BACKGROUND OF THE NEW PLANT

The present invention comprises a new and distinct cultivar of *Aglaonema,* botanically known as *Aglaonema* hybrid, and hereinafter referred to by the cultivar name 'TWYAG0009B'. The new cultivar originated from an open pollination made in Bogor, West Java, Indonesia. A single plant selection was chosen for further evaluation and for asexual propagation from the progeny of the open pollination in Bogor, W. Java, Indonesia.

The new cultivar was created in Bogor, W. Java, Indonesia and has been asexually reproduced repeatedly by vegetative cuttings and tissue culture in Apopka, Fla. The present invention has been found to retain its distinctive characteristics through successive asexual propagations.

Plant Breeder's Rights for this cultivar were applied for in the European Union in early September 2007. 'TWYAG0009B' has not been made publicly available more than one year prior to the filing of this application.

SUMMARY OF THE INVENTION

The following are the most outstanding and distinguishing characteristics of this new cultivar when grown under normal horticultural practices in Apopka, Fla.

1. Small to intermediate in stature;
2. Very dense, leafy, compact and upright branched growth habit;
3. Very vigorous; and
4. Somewhat faster growing than typical commercial *Aglaonema* cultivars.

DESCRIPTION OF PHOTOGRAPHS

This new *Aglaonema* plant is illustrated by the accompanying photographs which show the overall habit of the new plant. The colors shown are as true as can be reasonably obtained by conventional photographic procedures.

DESCRIPTION OF THE NEW CULTIVAR

Figure 1:
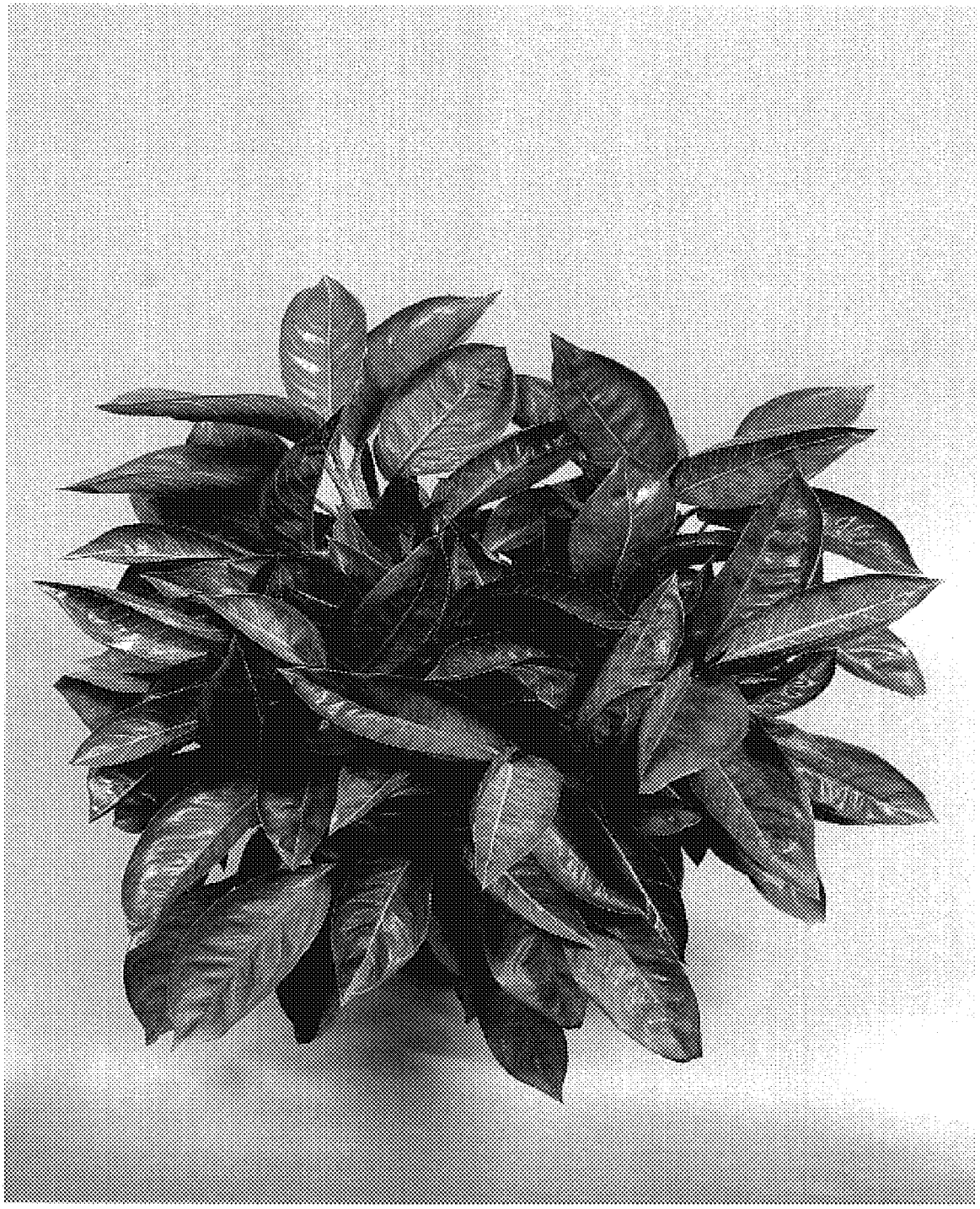
FIG. 1 shows the overall habit of the new plant.
Figure 2:
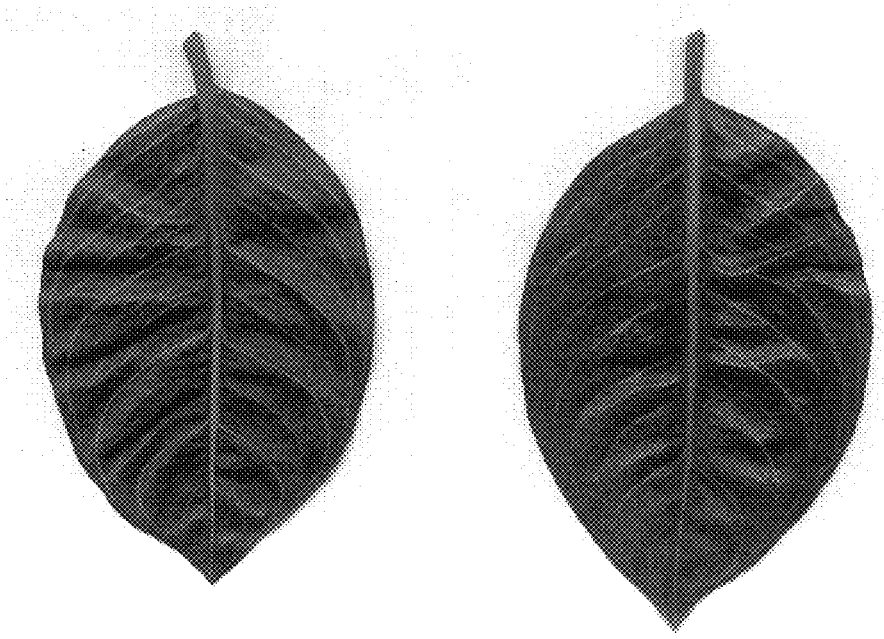
FIG. 2 shows the upper and lower surface of a new leaf.
Figure 3:
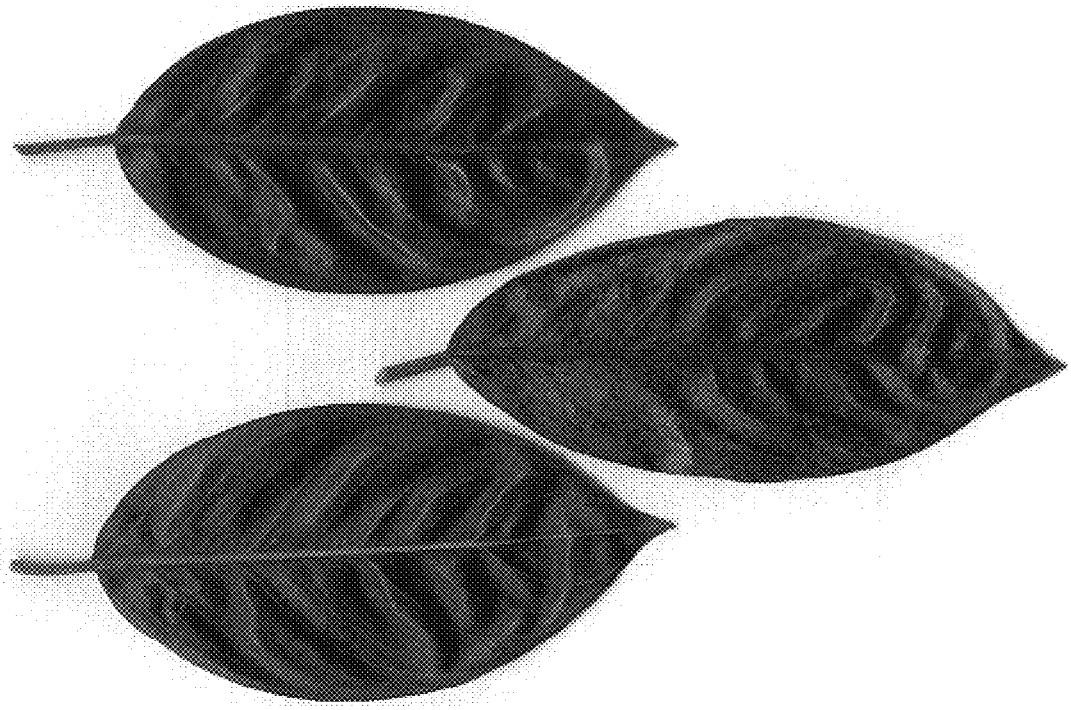
FIG. 3 shows the upper and lower surfaces of mature leaves.

The following detailed description sets forth the distinctive characteristics of 'TWYAG0009B'. The data which define these characteristics were collected from asexual reproductions carried out in Apopka, Fla. The plant history was taken on 18-month-old plants started from a single 4-leaf rooted cutting, still in a vegetative state and grown in Apopka, Fla. Rooted cuttings were planted in 20-cm pots and grown in a greenhouse in July 2006 where the average day temperature ranged from about 85° to 95° F. and the average night temperature ranged from about 72° to 78° F. The light level was about 3000 foot candles. The plants were pinched twice. Color readings were taken under natural light. Color referent primarily to the R.H.S. Colour Chart of The Royal Horticultural Society of London (R.H.S.) (2001).

DETAILED BOTANICAL DESCRIPTION

Classification:
*Family.*—*Araceae.*
*Botanical.*—*Aglaonema* hybrid.
*Cultivar name.*—'TWYAG0009B'.
*Common name.*—Chinese Evergreen.

Parentage: Unknown individual plants of *Aglaonema.*

Growth:
*Form.*—Symmetrical, wider than tall; new leaves held upright, mature leaves arch outward.
*Growth and branching habit.*—Very dense, leafy, compact; upright branched growth habit (basal branching); small to intermediate in stature.
*Height* (*from soil to top of leaf plane.*).—30 cm to 35 cm.
*Diameter* (*area of spread, measured from leaf tip to leaf tip across the canopy*).—44 cm to 50 cm.

*Time to produce a finished plant.*—18 months starting from a single 4-leaf rooted cutting and pinched twice.

*Root description.*—Abundant, fleshy white roots with finer lateral branches.

*Number of divisions or clumps per year.*—About 15, four-leaf cuttings per year.

*Durability of foliage to stresses.*—Leaves hold up well against damage from shipping and handling; plant is durable, excellent indoor keeping quality.

*High temperature tolerance.*—To about 104° F. for several hours without damage.

*Low temperature tolerance.*—To about 55° F. or several hours without damage.

Stems:

*Type.*—Basal branching.

*Number of branches per plant.*—49.

*Length* (*from soil line to the junction of the newest two leaves*).—17 cm.

*Diameter* (*measured from the midpoint*).—1.0 cm.

*Internode length.*—1.0 cm to 1.6 cm.

*Color.*—Immature: RHS 146C to RHS 146D tinged with RHS 146B, and mottled with RHS 160C. Mature: RHS 147A mottled with RHS 146C and tinged with RHS 163C.

*Appearance* (*shape*).—Columnar, cylindrical upright.

*Aspect.*—Vertical, upright.

*Strength.*—Sturdy, somewhat flexible.

*Axillary buds.*—Shape: Elliptic, flat. Length: 0.6 cm. Width: 0.35 cm. Color: RHS N155C.

Leaves:

*Arrangement.*—Alternate, single leaf per petiole, simple, arranged in a spiral along the stem.

*Quantity of leaves per stem.*—About 10–13.

*Length.*—12.8 cm to 14.9 cm.

*Width.*—Flattened: 6.5 cm to 7.5 cm. Not flattened: 5.0 cm to 6.5 cm; the leaf blade folds upward along the midrib.

*Shape.*—Elliptic.

*Apex.*—Acuminate.

*Base.*—Acute.

*Margin.*—Smooth, entire with some broad undulations.

*Texture, upper and lower surfaces.*—Smooth; new leaves shiny; mature leaves glossy to dull; the leaf blade is convex between the main veins giving the leaf a textured appearance; leaf blade (distal end) is cupped upward.

*Pubescence.*—None.

*Young leaf* (*newly expanded leaf*).—Color: Upper side: RHS 147A base color; leaf blade variably marked with irregular, diffuse RHS 147C and RHS 146A (lighter green) variegation. Lower side: RHS 147B base color with RHS 181C cast overall; leaf blade variably marked with irregular, diffuse RHS 147B (lighter-green) variegation.

*Mature leaf.*—Color: Upper side: Between RHS N189A and RHS 147A base color; leaf blade variably marked with irregular, diffuse RHS N189B, RHS 147A and RHS 191A (lighter green to grey-green) variegation; the variegation becomes more prominent as the leaf ages. Lower side: Between RHS 147A and RHS N189A base color with RHS 182B cast overall; leaf blade variably marked with irregular, diffuse RHS 147B, RHS 148A and RHS 191A (lighter green to grey-green) variegation; variegation becomes more prominent as the leaf ages.

*Venation pattern.*—Pinnate, radiating outward from the midrib in a herringbone arrangement.

*Venation color* (*newly expanded leaf*).—Upper surface: Primary veins: RHS 145C variably tinged with RHS 50C. Midrib: RHS 194D variably tinged with RHS 51C to RHS 51D. Lower surface: Primary veins: Between RHS 185D and RHS 181D. Midrib-proximal: Between RHS 147B and RHS 146B with faint spots of RHS 165D. Midrib-distal: RHS 181D.

*Venation color* (*mature leaf*).— *Upper surface: Primary veins:* RHS 147A to RHS 147B. Midrib: RHS 185C to RHS 185D with streaks of RHS 147A. Lower surface: Primary veins: RHS 65D tinged with RHS 195C. Midrib-proximal: RHS 147A to RHS 147B with faint spots of RHS 165D. Midrib-distal: RHS 65C to RHS 65D tinged with RHS 147B and RHS 146B.

Petioles:

*Aspect.*—Vertical, upright when newly expanded, becoming curved outward and about 45° with maturity.

*Length.*—7.0 cm.

*Diameter.*—Distal: 0.4 cm. Proximal (petiole and petiole sheath clasp the stem proximally): Flattened: 2.9 cm. Natural diameter: 1.0 cm.

*Color.*—Distal: Mottled with RHS 147A, RHS 146A and RHS 162D, tinged with RHS 147C (between top of wing and base of leaf). Proximal: Variably mottled or streaked with RHS 147A, RHS 146A, RHS 146B, RHS 161D and RHS N155C, and often tinged with RHS 49D.

*Wing length.*—6.2 cm.

*Wing diameter.*—Mid-point: 0.7 cm. Base: 1.0 cm. Depth: 0.55 cm.

*Wing color.*—Inside: RHS N155C sparsely mottled with RHS 146B. Outside: Variably mottled or streaked with RHS 147A, RHS 146A, RHS 146B, RHS 161D and RHS N155C and often tinged with RHS 49D. Area adjacent to stem: RHS N155C.

Inflorescence: None observed.

Fruit and seed set: None observed.

Disease and insect resistance: Typical of *Aglaonema;* no particular resistance or susceptibility noted.

COMPARISON WITH KNOWN CULTIVARS

'TWYAG0009B' differs from the commercial variety 'Key Largo' (U.S. Plant Pat. No. 17,550) in that 'TWYAG0009B' has a shorter and narrower growth habit than 'Key Largo'. In addition, the leaves of 'TWYAG0009B' are shorter, narrower and more variegated than the leaves of 'Key Largo'.

I claim:

1. A new and distinct cultivar of *Aglaonema* plant as shown and described herein.

* * * * *